United States Patent
Joglekar

(10) Patent No.: US 8,292,842 B2
(45) Date of Patent: Oct. 23, 2012

(54) AUTOMATICALLY INDENTIFYING THERAPY DELIVERY COMPONENT CONNECTED TO IMPLANTABLE MEDICAL DEVICE

(75) Inventor: Ajinkya M. Joglekar, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/072,021

(22) Filed: Mar. 25, 2011

(65) Prior Publication Data
US 2012/0245514 A1 Sep. 27, 2012

(51) Int. Cl.
*A61M 31/00* (2006.01)
(52) U.S. Cl. .......................................................... 604/67
(58) Field of Classification Search ............. 604/65–67, 604/131, 905; 128/DIG. 12, DIG. 13
See application file for complete search history.

(56) References Cited

U.S. PATENT DOCUMENTS

| 6,039,724 A * | 3/2000 | Seifert et al. ................... 604/533 |
| 6,385,593 B2 | 5/2002 | Linberg |
| 6,675,049 B2 | 1/2004 | Thompson et al. |
| 7,076,303 B2 | 7/2006 | Linberg |
| 7,239,916 B2 | 7/2007 | Thompson et al. |
| 7,429,920 B2 | 9/2008 | Smythe et al. |
| 7,474,223 B2 | 1/2009 | Nycz et al. |
| 7,518,502 B2 | 4/2009 | Austin et al. |
| 2002/0040234 A1 | 4/2002 | Linberg |
| 2004/0073266 A1 | 4/2004 | Haefner et al. |
| 2007/0018810 A1 | 1/2007 | Smythe et al. |

* cited by examiner

*Primary Examiner* — Manuel Mendez
(74) *Attorney, Agent, or Firm* — Shumaker & Sieffert, PA

(57) ABSTRACT

A therapy delivery component is connected to an IMD with a coupling that has a known physical property, based upon which the type and/or connection status of the therapy delivery component is automatically identified.

27 Claims, 9 Drawing Sheets

US 8,292,842 B2

AUTOMATICALLY INDENTIFYING THERAPY DELIVERY COMPONENT CONNECTED TO IMPLANTABLE MEDICAL DEVICE

TECHNICAL FIELD

This disclosure relates to implantable medical devices.

BACKGROUND

A variety of medical devices are used for chronic, i.e., long-term, delivery of fluid therapy to patients suffering from a variety of conditions, such as chronic pain, tremor, Parkinson's disease, epilepsy, urinary or fecal incontinence, sexual dysfunction, obesity, spasticity, or gastroparesis. For example, pumps or other fluid delivery devices can be used for chronic delivery of therapeutic fluids, such as drugs to patients. These devices are intended to provide a patient with a therapeutic output to alleviate or assist with a variety of conditions. Typically, such devices are implanted in a patient and provide a therapeutic output under specified conditions on a recurring basis.

One type of implantable fluid delivery device is a drug infusion device that can deliver a drug or other therapeutic fluid to a patient at a selected site. A drug infusion device may be partially or completely implanted at a location in the body of a patient and deliver a fluid medication through a catheter to a selected delivery site in the body. Drug infusion devices, such as implantable drug pumps, commonly include a reservoir for holding a supply of the therapeutic fluid, such as a drug, for delivery to a site in the patient. The fluid reservoir can be self-sealing and accessible through one or more ports. A pump is fluidly coupled to the reservoir for delivering the therapeutic fluid to the patient. A catheter provides a pathway for delivering the therapeutic fluid from the pump to a delivery site in the patient.

SUMMARY

In general, this disclosure describes techniques for automatically identifying the type and/or connection status of a therapy delivery component connected to an implantable medical device (IMD). In one example, a system includes an IMD, a therapy delivery component, a coupling, and a measurement circuit. The therapy delivery component is configured to deliver therapy to a patient. The coupling connects the therapy delivery component to a housing of the IMD. The measurement circuit is configured to apply an electrical input across the coupling and identify the therapy delivery component based on an electrical signal generated as an output upon application of the input across the coupling.

In another example, a method includes applying an electrical input across a coupling between an implantable medical device (IMD) and a therapy delivery component configured to deliver therapy to a patient, generating an electrical signal as an output to the electrical input applied across the coupling, and identifying the therapy delivery component based on the electrical signal.

In another example, a system includes means for applying an electrical input across a coupling between an implantable medical device (IMD) and a therapy delivery component configured to deliver therapy to a patient, means for generating an electrical signal as an output to the electrical input applied across the coupling between an implantable medical device (IMD) and a therapy delivery component configured to deliver therapy to tissue of a patient, and means for identifying the therapy delivery component based on the electrical signal.

In another example, a system includes an IMD, a therapy delivery component, a coupling, and a measurement circuit. The therapy delivery component is configured to deliver therapy to a patient. The coupling connects the therapy delivery component to the IMD. The measurement circuit is configured to apply an electrical input across the coupling and identify a connection status between the IMD and the therapy delivery component based on an electrical signal generated as an output upon application of the input across the coupling.

In another example, a method includes applying an electrical input across a coupling between an implantable medical device (IMD) and a therapy delivery component configured to deliver therapy to a patient. generating an electrical signal as an output to the electrical input applied across the coupling, and identifying a connection status between the IMD and the therapy delivery component based on the electrical signal.

In another example, a system includes means for applying an electrical input across a coupling between an implantable medical device (IMD) and a therapy delivery component configured to deliver therapy to a patient, means for generating an electrical signal as an output to the electrical input applied across the coupling between an implantable medical device (IMD) and a therapy delivery component configured to deliver therapy to tissue of a patient, and means for identifying a connection status between the IMD and the therapy delivery component based on the electrical signal.

The details of one or more examples disclosed herein are set forth in the accompanying drawings and the description below. Other features, objects, and advantages will be apparent from the description and drawings, and from the claims.

DETAILED DESCRIPTION

IMDs, including, e.g. therapeutic fluid delivery devices and electrical stimulation devices, commonly include the actual implantable device, including, e.g., a housing containing a battery, device circuitry, in the case of fluid delivery devices, a therapeutic fluid reservoir and a pumping mechanism, in the case of stimulation devices, a pulse generator, and a therapy delivery component, e.g. a catheter and/or a stimulation lead to deliver therapy to a point of interest within a patient. In some examples, both the IMD and the therapy delivery component are implanted and the IMD, e.g. a processor of the device is programmed to deliver the appropriate therapy to a patient via the delivery component.

Following implantation during initial and subsequent programming sessions, a user, e.g., a clinician, is required to select the correct therapy delivery component prior to programming the therapy. A therapy delivery component may be, for example, a catheter or electrical lead. For example, the user may be required to select the correct model number and configuration of the catheter or lead implanted within the patient prior to programming the therapy. Selecting the type of therapy delivery component actually implanted is an important step in delivering effective therapy to the patient. However, dependency on user selection makes the process susceptible to human error. The selection process can also be time consuming. For example, where the therapy delivery component information is not available, the clinician may have to follow a number of time consuming steps to obtain the information, including, e.g. calling technical services or taking a fluoroscopic image (for compatible therapy delivery components). In view of the foregoing manual, time consuming, and error prone processes, this disclosure describes techniques for automatically identifying the type of therapy delivery component connected to an IMD.

Figure 1:
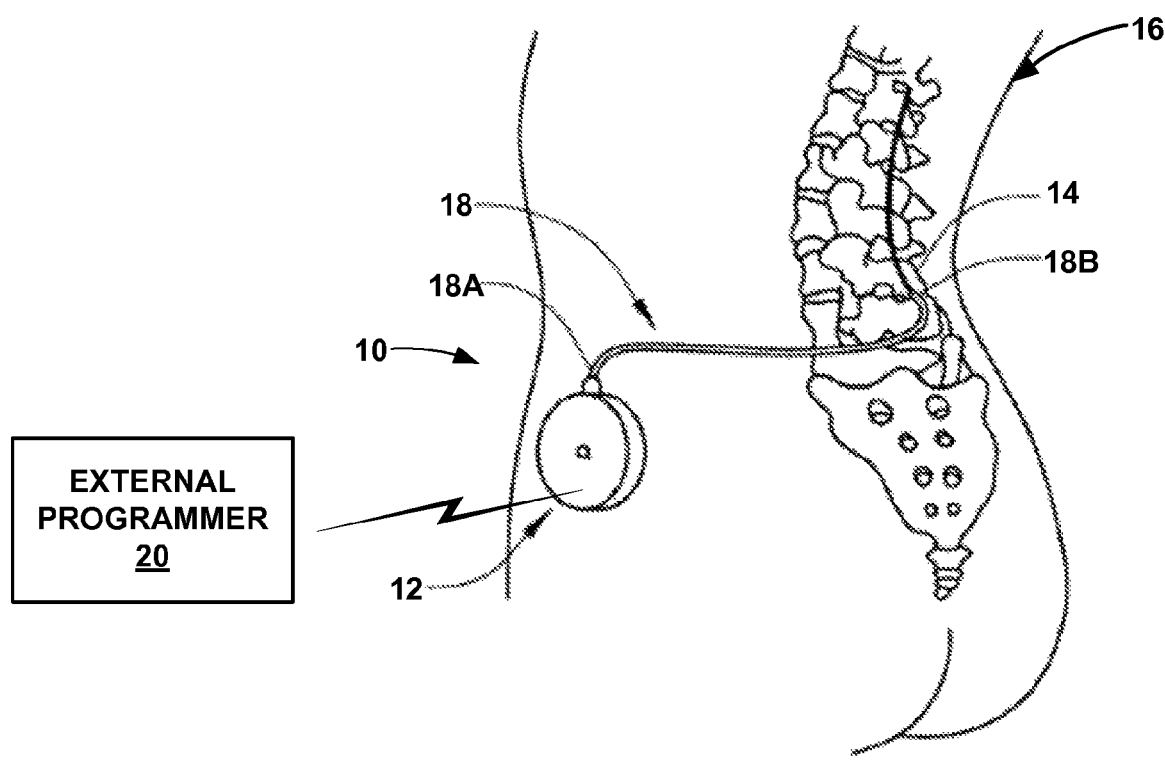
FIG. 1 is a conceptual diagram illustrating an example of a fluid delivery system including an implantable fluid delivery device configured to deliver a therapeutic fluid to a patient via a catheter.

FIG. 1 is a conceptual diagram illustrating an example of a therapy system 10, which includes IMD 12, a therapy delivery component, which, in the example of FIG. 1 is catheter 18, and external programmer 20. IMD 12 is connected to catheter 18 to deliver at least one therapeutic fluid, e.g. a pharmaceutical agent, pain relieving agent, anti-inflammatory agent, gene therapy agent, or the like, to a target site within patient 16. IMD 12 includes an outer housing that, in some examples, is constructed of a biocompatible material that resists corrosion and degradation from bodily fluids including, e.g., titanium or biologically inert polymers. IMD 12 may be implanted within a subcutaneous pocket relatively close to the therapy delivery site. For example, in the example shown in FIG. 1, IMD 12 is implanted within an abdomen of patient 16. In other examples, IMD 12 may be implanted within other suitable sites within patient 16, which may depend, for example, on the target site within patient 16 for the delivery of the therapeutic fluid. In still other examples, IMD 12 may be external to patient 16 with a percutaneous catheter connected between IMD 12 and the target delivery site within patient 16.

IMD 12 delivers a therapeutic fluid from a reservoir (not shown) to patient 16 through catheter 18 from proximal end 18A coupled to IMD 12 to distal end 18B located proximate to the target site. Example therapeutic fluids that may be delivered by IMD 12 include, e.g., insulin, morphine, hydromorphone, bupivacaine, clonidine, other analgesics, baclofen and other muscle relaxers and antispastic agents, genetic agents, antibiotics, nutritional fluids, hormones or hormonal drugs, gene therapy drugs, anticoagulants, cardiovascular medications or chemotherapeutics.

Catheter 18 can comprise a unitary catheter or a plurality of catheter segments connected together to form an overall catheter length. External programmer 20 is configured to wirelessly communicate with IMD 12 as needed, such as to provide or retrieve therapy information or control aspects of therapy delivery (e.g., modify the therapy parameters such as rate or timing of delivery, turn IMD 12 on or off, and so forth) from IMD 12 to patient 16.

Catheter 18 may be coupled to IMD 12 either directly or with the aid of a catheter extension (not shown in FIG. 1). In the example shown in FIG. 1, catheter 18 traverses from the implant site of IMD 12 to one or more targets proximate to spinal cord 14. Catheter 18 is positioned such that one or more fluid delivery outlets (not shown in FIG. 1) of catheter 18 are proximate to the targets within patient 16. In the example of FIG. 1, IMD 12 delivers a therapeutic fluid through catheter 18 to targets proximate to spinal cord 14.

IMD 12 can be configured for intrathecal drug delivery into the intrathecal space, as well as epidural delivery into the epidural space, both of which surround spinal cord 14. In some examples, multiple catheters may be coupled to IMD 12 to target the same or different nerve or other tissue sites within patient 16, or catheter 18 may include multiple lumens to deliver multiple therapeutic fluids to the patient. Therefore, although the target site shown in FIG. 1 is proximate to spinal cord 14 of patient 16, other applications of therapy system 10 include alternative target delivery sites in addition to or in lieu of the spinal cord of the patient.

Programmer 20 is an external computing device that is configured to communicate with IMD 12 by wireless telemetry. For example, programmer 20 may be a clinician programmer that the clinician uses to communicate with IMD 12 and program therapy delivered by the IMD. Alternatively, programmer 20 may be a patient programmer that allows patient 16 to view and modify therapy parameters associated with therapy programs. The clinician programmer may include additional or alternative programming features than the patient programmer. For example, more complex or sensitive tasks may only be allowed by the clinician programmer to prevent patient 16 from making undesired or unsafe changes to the operation of IMD 12. Programmer 20 may be a handheld or other dedicated computing device, or a larger workstation or a separate application within another multi-function device.

As described in greater detail below, in examples according to this disclosure, a therapy delivery component is connected to an IMD with a coupling that has a known physical property, e.g. electrical resistance or capacitance, based upon which the type and particular configuration of the therapy delivery component may be identified. For example, the therapy delivery component of system 10 of FIG. 1, i.e. catheter 18 may be connected to IMD 12 with a coupling that has a known electrical resistance. In one example, connecting the catheter to the IMD with the coupling closes a circuit that may apply an electrical input, e.g., a predetermined measurement current across the coupling. The type and particular configuration of catheter 18 may, in turn, be identified based on a signal generated as an output in response to the input applied across the coupling between the catheter and IMD 12. For example, the type and configuration of catheter 18 may be identified based on a voltage signal generated as an output to the current input applied across the coupling with the known resistance. The voltage signal generally will be linearly proportional to the resistance.

As used in this disclosure, coupling refers to a structure or a number of structures that connect an IMD and a therapy delivery component. The term coupling, alone, does not denote any specific structure for achieving the function of connecting the IMD to the therapy delivery component. As such, other terms could be used to describe a coupling within the meaning of this disclosure, including, e.g. connection, connector, junction, joint, fastener, clasp and link.

In one example, the coupling between catheter 18 and IMD 12 in the example of FIG. 1 may include a first connector connected to proximal end 18A of the catheter. Some part or all of the first connector connected to end 18A of catheter 18 may include, e.g., a known electrical resistance. The coupling may also include a second connector connected to IMD 12 and measurement circuit included in the IMD. The second connector is configured to receive the connector connected to end 18A of catheter 18. In such an example, connecting the first connector connected to end 18A of catheter 18 with the second connector connected to IMD 12 may close a circuit between the coupling and the measurement circuit of the IMD 12. The measurement circuit may apply an electrical input across the coupling, the application of which generates a voltage signal as an output. The measurement circuit of IMD 12 may then identify the type of therapy delivery component based on the voltage.

For example, the measurement circuit may measure the voltage output signal and transmit the signal to a processor of IMD 12, e.g., via an analog-to-digital converter (ADC), which converts the signal to a digital value. The processor then may identify the time of circuit based on the digital value, e.g., by comparing the digital value to one or more digital threshold values. The processor of IMD 12 may then cross-reference the voltage value in a look-up table or other organized aggregation of data of therapy delivery components and associated voltages stored on memory of the IMD or another device, e.g. programmer 20. In another example, the measurement circuit may identify the type and configuration of catheter 18 by calculating the resistance of the first connector from the voltage. For example, the measurement circuit may measure the voltage output signal and transmit the value to a processor of IMD 12, which processor may, in turn, calculate the resistance of the first connector from the voltage generated by the coupling between the IMD and catheter 18 and search for the resistance in a look-up table or other organized aggregation of data of therapy delivery components and associated resistances stored on memory of the IMD or another device, e.g. programmer 20. As a further alternative, in some examples, an analog comparator or other circuit associated with the measurement circuit may compare the signal to threshold voltage to generate an indication of the type of catheter, and communicate the signal to the processor, e.g., via an ADC.

In other examples, the first connector of the coupling between catheter 18 and IMD 12 may include a known capacitance instead of resistance, by which, in a similar fashion as described in the foregoing example, the type and particular configuration of the catheter connected to the IMD may be identified. Additional configurations of the coupling between a therapy delivery component and an IMD are described below with reference to FIG. 3.

Figure 2:
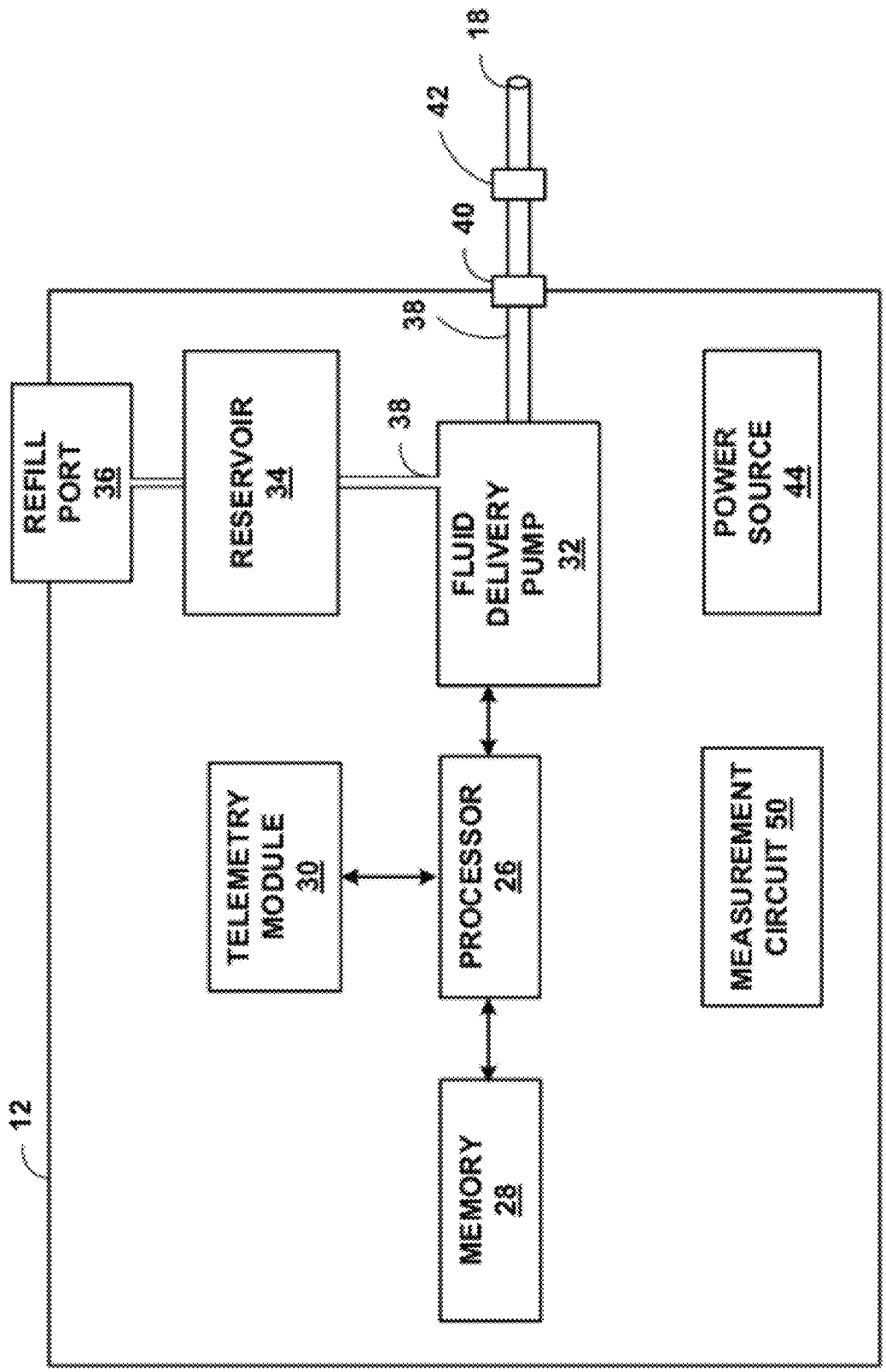
FIG. 2 is functional block diagram illustrating an example of the implantable fluid delivery device and catheter of FIG. 1.

FIG. 2 is a functional block diagram illustrating components of an example of IMD 12, which includes processor 26, memory 28, telemetry module 30, fluid delivery pump 32, reservoir 34, refill port 36, internal tubing 38, catheter access port 40, coupling 42, power source 44, and measurement circuit 50. Processor 26 is communicatively connected to memory 28, telemetry module 30, and fluid delivery pump 32. Fluid delivery pump 32 is connected to reservoir 34 and internal tubing 38. Reservoir 34 is connected to refill port 36. Catheter access port 40 is connected to internal tubing 38 and catheter 18.

IMD 12 also includes power source 44, which is configured to deliver operating power to various components of the IMD. In some examples, IMD 12 may include a number of reservoirs for storing more than one type of therapeutic fluid. In some examples, IMD 12 may include a single long tube that contains the therapeutic fluid in place of a reservoir. However, for ease of description, an IMD 12 including a single reservoir 34 is primarily described with reference to the disclosed examples.

During operation of IMD 12, processor 26 controls fluid delivery pump 32 with the aid of instructions associated with program information that is stored in memory 28 to deliver a therapeutic fluid to patient 16 via catheter 18. Instructions executed by processor 26 may, for example, define therapy programs that specify the dose of therapeutic fluid that is delivered to a target tissue site within patient 16 from reservoir 30 via catheter 18. The programs may further specify a schedule of different therapeutic fluid rates and/or other parameters by which IMD 12 delivers therapy to patient 16.

In general, a therapy program stored on memory 28 and executed by processor 26 defines one or more therapeutic fluid doses to be delivered from reservoir 34 to patient 16 through catheter 18 by IMD 12. A dose of therapeutic fluid generally refers to a total amount of therapeutic fluid, e.g., measured in milligrams or other volumetric units, delivered over a total amount of time, e.g., per day or twenty-four hour period. The amount of therapeutic fluid in a dose may convey to a caregiver an indication of the probable efficacy of the fluid and the possibility of side effects.

In general, a sufficient amount of the fluid should be administered in order to have a desired therapeutic effect, such as pain relief. However, the amount of the therapeutic fluid delivered to the patient should be limited to a maximum amount, such as a maximum daily amount, in order not to avoid potential side effects. Therapy program parameters specified by a user, e.g., via programmer 20 may include fluid volume per dose, dose time period, maximum dose for a given time interval e.g., daily. In some examples, dosage may also prescribe particular concentrations of active ingredients in the therapeutic fluid delivered by IMD 12 to patient 16.

The manner in which a dose of therapeutic fluid is delivered to patient 16 by IMD 12 may also be defined in the therapy program. For example, processor 26 of IMD 12 may be programmed to deliver a dose of therapeutic fluid according to a schedule that defines different rates at which the fluid is to be delivered at different times during the dose period, e.g. a twenty-four hour period. The therapeutic fluid rate refers to the amount, e.g. in volume, of therapeutic fluid delivered over a unit period of time, which may change over the course of the day as IMD 12 delivers the dose of fluid to patient 16.

As an example, IMD 12 could be programmed to deliver therapeutic fluid to patient 16 at a rate of 20 microliters per hour. In the event the therapy program prescribes this fluid delivery rate for a twenty four hour period and assuming no patient or other boluses during the period of time, the dose of fluid delivered to patient 16 by IMD 12 will be 480 microliters (per twenty four hours). The therapy program may include other parameters, including, e.g., definitions of priming and patient boluses, as well as time intervals between successive patient boluses, sometimes referred to as lock-out intervals.

Therapy programs may be a part of a program group, where the group includes a number of therapy programs. Memory 28 of IMD 12 may store one or more therapy programs, as well as instructions defining the extent to which patient 16 may adjust therapy parameters, switch between therapy programs, or undertake other therapy adjustments. Patient 16 or a clinician may select and/or generate additional therapy programs for use by IMD 12, e.g., via external programmer 20 at any time during therapy or as designated by the clinician.

Components described as processors within IMD 12, external programmer 20, or any other device described in this disclosure may each include one or more processors, such as one or more microprocessors, digital signal processors (DSPs), application specific integrated circuits (ASICs), field programmable gate arrays (FPGAs), programmable logic circuitry, or the like, either alone or in any suitable combination.

In one example, processor 26 of IMD 12 is programmed to deliver a dose of therapeutic fluid to patient 16, which is defined in memory 28 of the device by a volume of therapeutic fluid delivered to the patient in one day. IMD 12 may also be programmed according to a therapy schedule such that the fluid is delivered at different rates at different times during the day, which may be stored in the device memory, e.g., as a look-up table associating different fluid rates at different times during the day.

Regardless of the particular manner in which IMD 12 is programmed to deliver a therapeutic fluid to patient 16, an important operational parameter of the IMD is the size and configuration of the therapy delivery component connected to the IMD, i.e. catheter 18 in the examples of FIGS. 1 and 2. For example, in order to program IMD 12, e.g. during a clinician guided programming session using, e.g., programmer 20, the clinician may need to identify catheter 18. For example, the size and configuration of catheter 18 may affect the rate, frequency, and volume of fluid delivered to patient 16.

Additionally, the size of catheter 18, e.g., the diameter of the lumen of the catheter may need to be known in order to properly calculate priming, bridge, supplemental, or other boluses. A priming bolus refers to a bolus delivered by IMD 12 to move the fluid to the distal tip 18B of catheter 18. A bridging bolus, which can also be referred to as a bridge is performed when a new fluid is inserted into a reservoir of IMD 12 while an old fluid is still present in the device, e.g., within internal tubing of the device and/or within catheter 18 connected to the device. The bridge is performed to define a rate at which to deliver the old fluid until the old fluid is completely delivered out of catheter 18 and to patient 16 such that IMD 12 contains only the new fluid. A supplemental bolus is a bolus administered to patient 16 outside of a programmed therapy schedule. The terms patient, independent, one-time, and therapeutic bolus may also be used in this disclosure to refer to a supplemental bolus. Errors in bolus definitions can lead to improper dosing of patient 16.

In the past, clinicians have commonly identified therapy delivery components connected to an IMD by manually selecting the type and configuration of the catheter from an array of possible types and configurations. However, manual identification is susceptible to human error, which may result in improperly identifying the therapy delivery component connected to the IMD, e.g. catheter 18 connected to IMD 12. As such, in examples according to this disclosure, a therapy delivery component is connected to an IMD with a coupling that is configured to generate a signal based upon which the type and particular configuration of the therapy delivery component may be identified.

Figure 3:
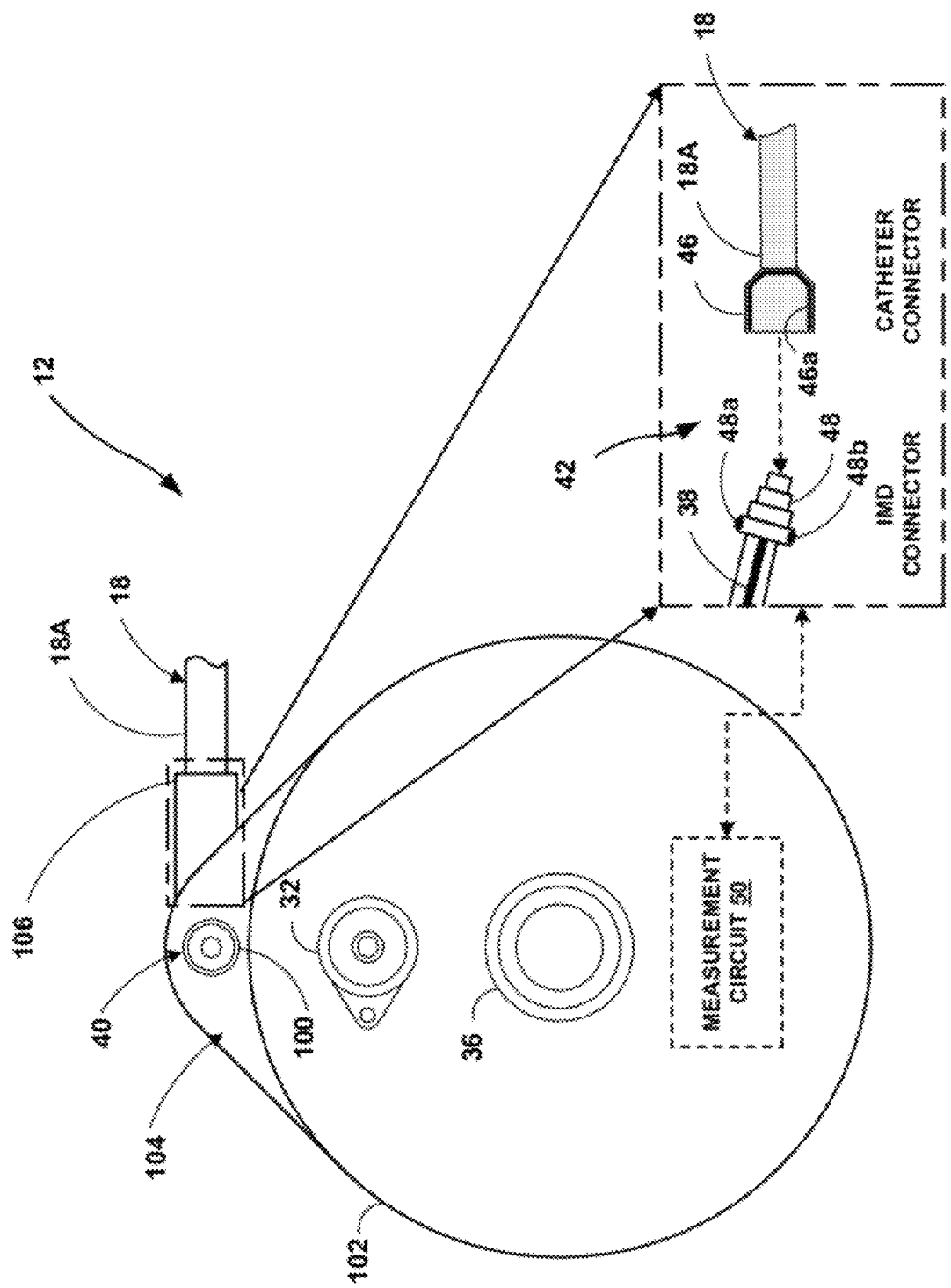
FIG. 3 is a plan view of an example configuration of an implantable fluid delivery device.
Figure 4A:
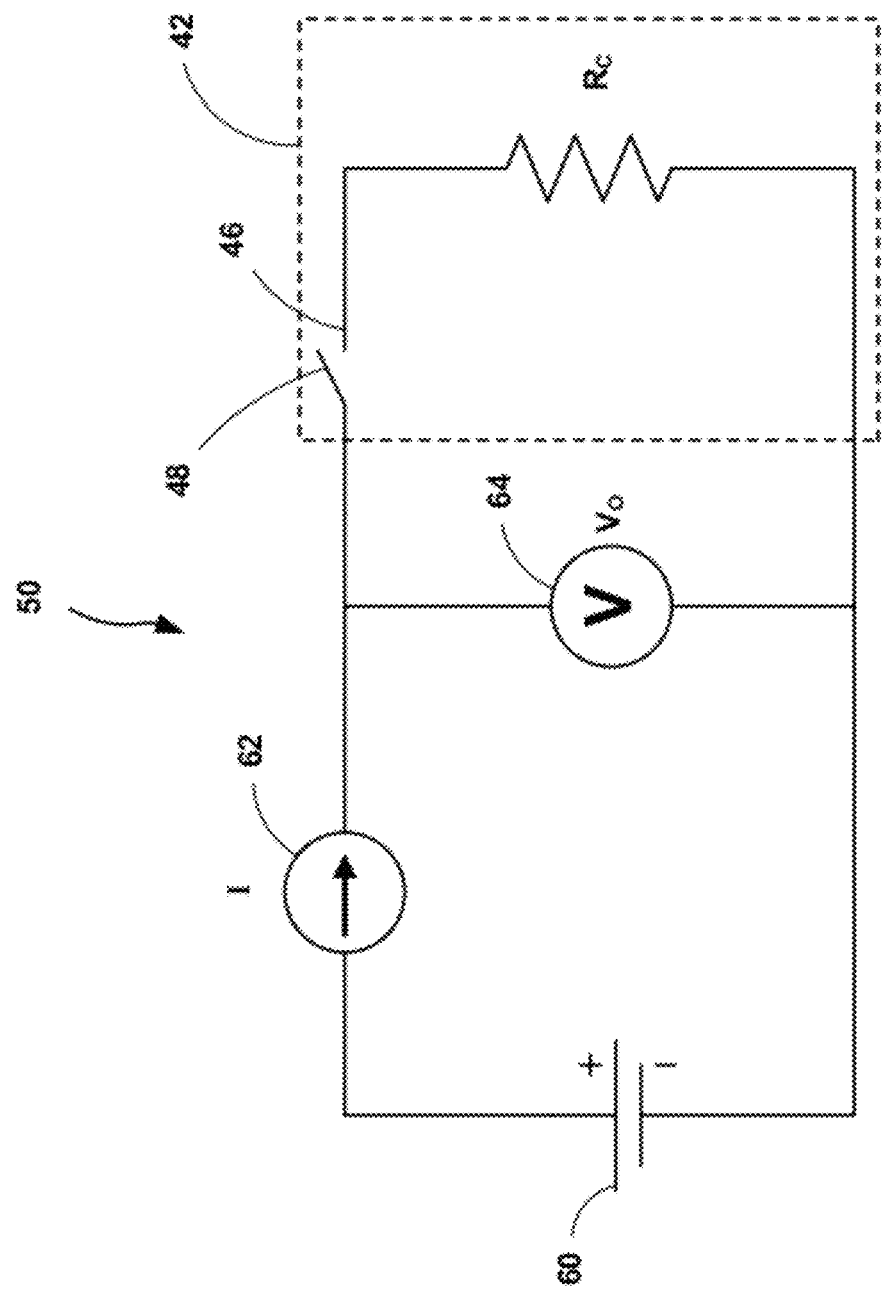
FIGS. 4A-4C are examples of measurement circuits that may be included in the implantable fluid delivery device of FIG. 3.
Figure 4B:
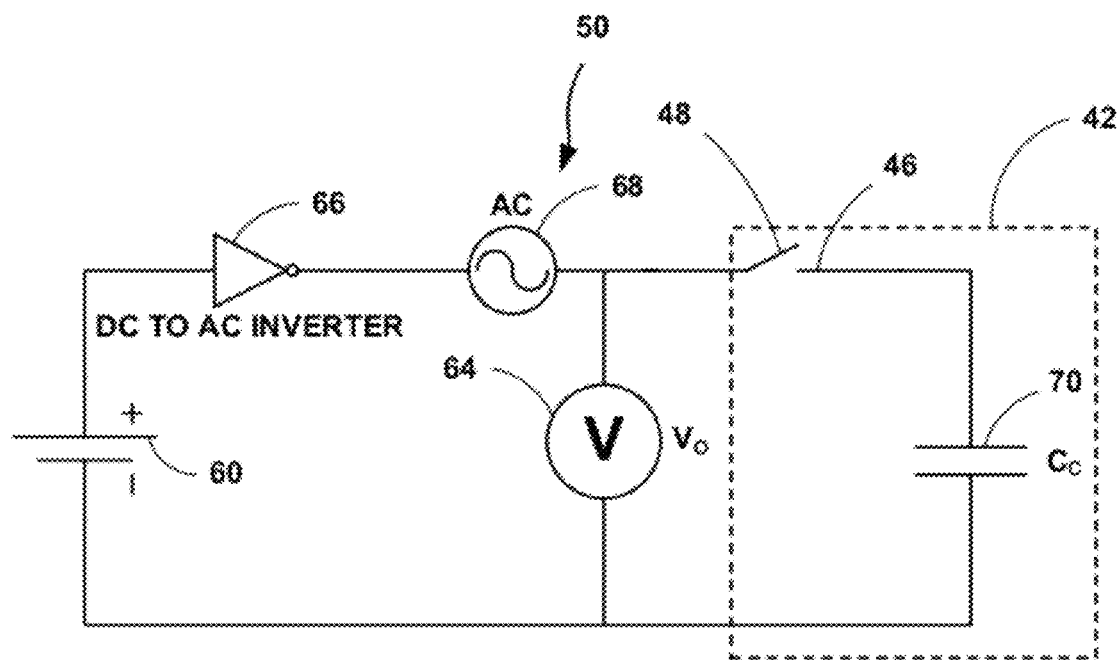
Figure 4C:
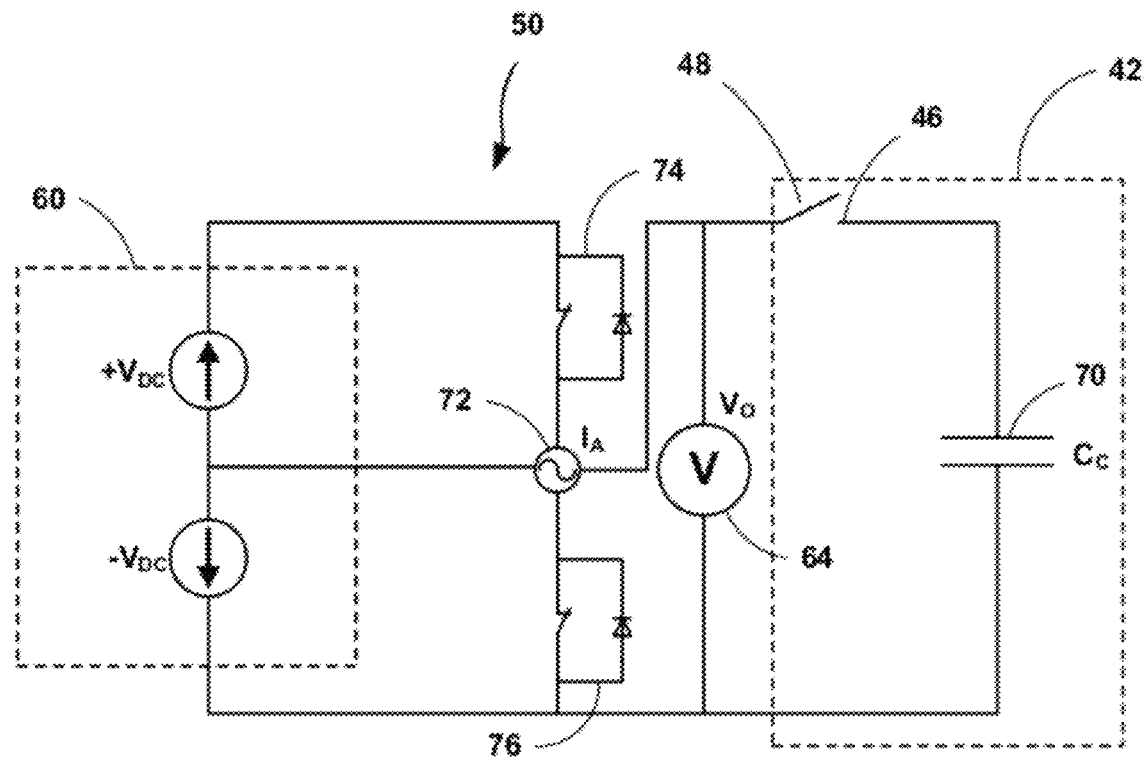

Measurement circuit 50, alone or in conjunction with other components, including, e.g., processor 26 of IMD 12 or a processor of programmer 20 or another device communicatively connected to IMD 12, may be configured to identify catheter 18 based on a signal generated as an output sensed in response to an electrical input applied across coupling 42 between the catheter and IMD 12. For example, the type and particular configuration of catheter 18 may be identified by processor 26 based on a signal generated as an output to an electrical input applied by measurement circuit 50 across coupling 42 when the catheter and IMD 12 are connected by the coupling. Upon identification of catheter 18, in one example, processor 26 may control telemetry module 30 to communicate the type and configuration of the therapy delivery component to programmer 20, e.g., for use by a clinician in programming IMD 12 to deliver therapy to patient 16. In addition to or in lieu of transmitting the type and configuration of catheter 18 to programmer 20, or another device communicatively connected to IMD 12, the IMD, and, in particular, e.g., processor 26 may store the information about the therapy delivery component on memory 28, and/or on memory of another device, e.g. programmer 20. An example configuration of IMD 12 including coupling 42 is illustrated in FIG. 3. Additionally, examples of measurement circuit 50 are illustrated in FIGS. 4A-4C.

FIG. 3 is a plan view of an example configuration of IMD 12 including catheter 18, fluid delivery pump 32, refill port 36, CAP 40, and CAP septum 100. IMD 12 includes housing 102 and header 104, which includes CAP 40 and CAP septum 100. In another example, however, CAP 40 and septum 100 may be arranged in another location in housing 102 of IMD 12. As described above, fluid delivery pump 32 is connected to CAP 40 by internal tubing 38 (not shown in FIG. 3). Fluid delivery pump 32 is also connected to catheter extension 106 via tubing 38 in header 104. Internal tubing 38 may be a segment of tubing or a series of cavities within IMD 12 that run from reservoir 34, around or through fluid delivery pump 32 to catheter access port 40. Catheter extension 106 is connected to proximal end 18A of catheter 18, from which the catheter extends from IMD 12 to the target delivery site within patient 16. In other examples, IMD 12 may not include catheter extension 106, in which case, catheter 18 may, e.g., be directly connected to tubing 38 in header 104 of the IMD.

Catheter 18 is connected to IMD 12 by coupling 42. In the example of FIG. 3, coupling 42 is incorporated into the connection between catheter 18 and extension 106. However, in other examples, catheter 18 may be connected directly to IMD 12 by coupling 42, or coupling 42 may connect catheter extension 106 to IMD 12, which, in turn, connects catheter 18 to the device. Regardless of the particular arrangement of IMD, therapy delivery component, and coupling, measurement circuit 50 of IMD 12 may be configured to identify catheter 18 based on a signal generated as an output to an electrical input applied by the circuit across coupling 42.

In the example of FIG. 3, coupling 42 includes first connector 46 connected to proximal end 18A of catheter 18. Coupling 42 also includes second connector 48 connected to IMD 12, e.g., to internal tubing 38 as shown in the example of FIG. 3. Second connector 48 of coupling 42 is configured to receive first connector 46 and is connected to measurement circuit 50 of IMD 12. For example, as illustrated in FIG. 3, second connector 48 of coupling 42 may include a male connector configured to receive female first connector 46 of the coupling. In another example, second connector 48 connected to IMD 12 may include a female connector configured to receive a male connector 46 connected to catheter 18. In any event, some part or all of first connector 46 connected to end 18A of catheter 18 and second connector 48 connected to IMD 12 may include an electrically conductive material. For example, first connector 46 may include conductor 46a and second connector 48 may include conductors 48a, 48b. Conductors 48a and 48b of second connector 48 are each independently connected to measurement circuit 50. Conductors 46a and 48a, 48b for first and second connectors 46, 48, respectively, may be formed of the same or different electrically conductive material or materials. For example, one or all of conductors 46a and 48a, 48b may be fabricated from copper, steel, or another electrically conductive metal. In some examples, one or both of conductors 46a and 48a may be fabricated from a biocompatible electrically conductive material, including, e.g., titanium, stainless steel, platinum or gold. In any event, connecting first connector 46 to second connector 48, and, in particular, connecting conductor 46a to two conductors 48a, 48b may act to complete measurement circuit 50 such that coupling a signal, e.g. voltage, current, resistance, or capacitance, is generated when measurement circuit applies an electrical input, e.g. a constant current or voltage, across coupling 42.

Different mechanical configurations of coupling 42, including first connector 46 and second connector 48 are possible in examples according to this disclosure. In one example, coupling 42 may be configured such that a mechanical coupling between connectors 46 and 48 also serves to close measurement circuit 50, e.g. via conductor 46a and conductors 48a, 48b. In such an example, the size, e.g. thickness, or other geometrical characteristic, or the material of the mechanical coupling 42 may be varied based on the type and configuration of catheter 18. In another example, however, coupling 42 may include a separate electrical connection for closing measurement circuit 50 from the mechanical coupling that physically connects proximal end 18A of catheter 18 to IMD 12. In this example, the size or material of the electrical connection that functions to close measurement circuit 50 when catheter 18 is connected to IMD 12 by coupling 42 may be varied based on the type and configuration of catheter 18. The mechanical or other coupling employed in coupling 42 may be fabricated from a variety of materials, including metals and plastics and may be incorporated into catheter 18 in a variety of ways, including, e.g., embedding the coupling in the wall of proximal end 18A of catheter 18. Various mechanical couplings may be employed in coupling 42, including threaded couplings, snap or press fit couplings, set screws, and the like.

Although the foregoing example includes identifying catheter 18 based on the physical properties of components contained completely within coupling 42, e.g. conductor 46a, in other examples, the catheter, or another therapy delivery component may be identified based on properties of components that are outside of or extend beyond the coupling between the catheter and IMD 12. For example, connecting IMD 12 and catheter 18 may complete measurement circuit 50 such that the circuit applies an electrical input, e.g. a measurement current through coupling 42 and across some conductive element contained in the catheter beyond the coupling, i.e. distal to the IMD and the coupling toward distal end 18B of the catheter.

FIG. 4A is a diagram illustrating an example of measurement circuit 50 of IMD 12 including battery 60, current source 62, voltmeter 64, and coupling 42, which includes first connector 46 and second connector 48. Measurement circuit 50 in FIG. 4A is intended for illustrative purposes and thus some of the details of the physical configuration of coupling 42, including, e.g. conductors 46a and 48a, 48b of first and second connectors 46, 48, respectively, have been omitted from the figure for simplicity. However, joining first and second connectors 46 and 48, respectively, of coupling 42 in FIG. 4A to complete measurement circuit 50 includes connecting conductor 46a to conductors 48a, 48b, as illustrated in FIG. 3. In FIG. 4A, battery 60 acts as a power source for measurement circuit 50. In one example, measurement circuit 50 may be connected to battery 44 of IMD 12, instead of including an additional separate power source. In any event, battery 60 supplies power to current source 62, which drives measurement circuit 50 with a known measurement current, I. Although FIG. 4A illustrates completing measurement circuit by connecting first and second connectors 46, 48, respectively, such that the circuit is connected to the positive and negative terminals of battery 60, in another example, one side of the circuit may be connected to a ground instead of the negative side of the battery or other power source employed in measurement circuit 50. In the example of FIG. 4A, connecting IMD 12 and catheter 18 via coupling 42 may act to complete measurement circuit 50 such that current, I, from current source 62 may flow across conductor 46, which includes a known resistance, $R_C$. Measurement circuit 50 also includes voltmeter 64. Voltmeter 64 may be configured to produce an output voltage signal, $V_O$, when current, I, from current source 62 is applied across coupling 42, and, in particular, across conductor 46 including resistance, $R_C$.

Measurement circuit 50 may then identify catheter 18 connected to IMD 12 based on the output voltage, $V_O$. For example, measurement circuit 50 may communicate output voltage, $V_O$, from voltmeter 64 to a processor as a digital voltage value, e.g. via an ADC. In another example, an analog comparator or other circuit associated with measurement circuit 50 may compare output voltage, $V_O$, from voltmeter 64 to a threshold voltage to generate an indication of the type of catheter, and communicate the signal to the processor, e.g., via an ADC. In one example, the processor and other digital components necessary to identify catheter 18 based on the analog electrical output signals generated by measurement circuit 50 may be included in the measurement circuit. In another example, however, measurement circuit 50 may communicate with, e.g., processor 26 and memory 28 in the process of identifying the type and configuration of catheter 18. In one example, processor 26 of IMD 12 cross-references the voltage, $V_O$, from voltmeter 64, e.g., in a look-up table or other organized aggregation of data of therapy delivery components and associated voltages stored on memory 28. In other words, in such an example, processor 26 identifies the type and configuration of catheter 18 connected to IMD 12 directly based on the output voltage, $V_O$, measured by voltmeter 64, which may have been previously mapped to different types of catheters with different known resistances. In another example, measurement circuit 50 may communicate the output voltage signal, $V_O$, from voltmeter 64 to processor 26, which may identify the type and configuration of catheter 18 by calculating the resistance, $R_C$, of conductor 46a of first connector 46 from the voltage. For example, processor 26 may calculate the resistance of conductor 46a of first connector 46 from the voltage, $V_O$, generated as an output to the input current, I, applied by current source 62 of measurement circuit 50 across coupling 42 and search for the resistance in a look-up table or other organized aggregation of data of therapy delivery components and associated resistances stored on memory 28 of the IMD 12, or memory of another device, e.g. programmer 20.

In one example, conductor 46a of first connector 46 connected to end 18A of catheter 18 is formed from a titanium alloy including an electrical resistivity of approximately $42 \times 10^{-8}$ ohm meters ($\Omega$m) or 42 micro ohm meters ($\mu\Omega$m). Catheter 18 is connected to IMD 12 via coupling 42 such that first connector 46, and, in particular, conductor 46a of the first connector is connected to conductor 48a of second connector 48, which completes measurement circuit 50 such that a voltage signal generated as an output to an input applied by the measurement circuit across coupling 42. Measurement circuit 50 communicates the output voltage signal to, e.g., processor 26 of IMD 12, or a processor of another device communicatively connected to the IMD, e.g. programmer 20, which, in turn, calculates the resistance, e.g. approximately 42 micro ohm meters ($\mu\Omega$m), of first connector 46 from the voltage signal generated by coupling 42. After calculating the resistance of titanium conductor 46a of first connector 46 from the voltage signal generated as an output to an input applied by measurement circuit 50 across coupling 42, processor 26 identifies catheter 18 by searching for the resistance in a look-up table of different types of therapy delivery components and associated resistances stored on memory 28 of the IMD or another device, e.g. programmer 20. For example, processor 26 identifies catheter 18 as a single lumen catheter with a stock length of approximately 89.0 centimeters and an inner diameter of approximately 0.053 centimeters. Processor 26 in conjunction with measurement circuit 50 need not identify the type and configuration of catheter 18, or, e.g. the connection status of the catheter, continually, but may make such identifications or other determinations periodically, e.g. in order to reduce the load on power source 44 of IMD 12 and thereby potentially increase the longevity of the device.

In some examples, measurement circuit 50, alone or in conjunction with other components, e.g. processor 26, or a processor of another device, may identify characteristics of catheter 18 other than those described above. In one example, measurement circuit may identify whether or not catheter 18 is safe for use with other medical equipment, including, e.g., a Magnetic Resonance Imaging (MRI) machine.

In addition to or in lieu of employing known resistances, some part or all of first connector 46 connected to end 18A of catheter 18 may include a known electrical capacitance. First connector 46 may include, in addition to conductor 46a, a dielectric material such that connecting first connector 46 and second connector 48 interposes the dielectric material between conductor 46a of the first connector and conductor 48a of the second connector. The dielectric material of first connector 46 may include a known capacitance. In such an example, connecting first connector 46 to second connector 48 may act to complete measurement circuit 50 such that a voltage signal is generated as an output to an electrical input, e.g. constant current, applied by the circuit across coupling 42. Measurement circuit 50, alone or in conjunction with, e.g. processor 26 of IMD 12, or a processor of another device communicatively connected to the IMD, e.g. programmer 20, may identify catheter 18 based on the voltage signal or, in one example, may calculate the capacitance of first connector 46, e.g. of the dielectric of the first connector from the voltage signal generated by coupling 42. In the latter case, after calculating the capacitance of first connector 46 from the voltage signal generated as an output of measurement circuit 50, processor 26, for example, may identify, e.g., the type and configuration of catheter 18 by, e.g., searching for the resistance in a look-up table or other organized aggregation of different types of therapy delivery components and associated resistances stored on memory 28 of IMD 12 or another device, e.g. programmer 20.

FIGS. 4B and 4C are diagrams illustrating two examples of measurement circuit 50 of IMD 12, in which some part or all of first connector 46 connected to end 18A of catheter 18 includes a known electrical capacitance. In order to employ capacitance as a means by which the type and configuration of catheter 18 is identified, it may be necessary to provide an alternating current (AC) source across coupling 42. As such, in the examples of FIGS. 4B and 4C two different mechanisms are employed to effectively convert DC battery 60 to an AC source as an electrical input across coupling 42.

The example of FIG. 4B illustrates measurement circuit 50 including battery 60, DC to AC inverter 66, AC source 68, voltmeter 64, and coupling 42, which includes first connector 46 and second connector 48. In the example of FIG. 4B, direct current from battery 60 is converted to alternating current via DC to AC inverter 66, thereby generating AC source 68. AC source 68 provides an alternating current input across coupling 42, which includes first connector 46 and second connector 48. First connector 46 includes capacitor 70, which may include a dielectric material, e.g. air, with a known capacitance. In such an example, connecting IMD 12 and catheter 18 via coupling 42 may act to complete measurement circuit 50 such that current from AC source 68 flows across connector 46, which includes a known capacitance, $C_C$. Measurement circuit 50 also includes voltmeter 64. Voltmeter 64 may be configured to produce an output voltage signal, $V_O$, when current from AC source 68 is applied across coupling 42, and, in particular, across conductor 46 including capacitance, $C_C$.

Measurement circuit 50 may then identify catheter 18 connected to IMD 12 based on the output voltage, $V_O$. For example, measurement circuit 50 may communicate output voltage, $V_O$, from voltmeter 64 to a processor as a digital voltage value, e.g. via an ADC. In another example, an analog comparator or other circuit associated with measurement circuit 50 may compare output voltage, $V_O$, from voltmeter 64 to a threshold voltage to generate an indication of the type of catheter, and communicate the signal to the processor, e.g., via an ADC. In one example, the processor and other digital components necessary to identify catheter 18 based on the analog electrical output signals generated by measurement circuit 50 may be included in the measurement circuit. In another example, however, measurement circuit 50 may communicate with, e.g., processor 26 and memory 28 in the process of identifying the type and configuration of catheter 18. In one example, processor 26 of IMD 12 cross-references the voltage, $V_O$, from voltmeter 64, e.g., in a look-up table or other organized aggregation of data of therapy delivery components and associated voltages stored on memory 28. In other words, in such an example, processor 26 identifies the type and configuration of catheter 18 connected to IMD 12 directly based on the output voltage, $V_O$, measured by voltmeter 64, which may have been previously mapped to different types of catheters with different known capacitances. In another example, measurement circuit 50 may communicate the output voltage signal, $V_O$, from voltmeter 64 to processor 26, which may identify the type and configuration of catheter 18 by calculating the capacitance, $C_C$, of capacitor 70 of first connector 46 from the voltage. For example, processor 26 may calculate the capacitance, $C_C$, of capacitor 70 of first connector 46 from the voltage, $V_O$, generated as an output to the input current applied by AC source 68 of measurement circuit 50 across coupling 42 and search for the capacitance in a look-up table or other organized aggregation of data of therapy delivery components and associated capacitances stored on memory 28 of the IMD 12, or memory of another device, e.g. programmer 20.

In the example of FIG. 4C, instead of employing DC to AC inverter 66 shown in FIG. 4B, measurement circuit 50 simulates an AC source by toggling between positive and negative sides of DC battery 60 over time. For example, in FIG. 4C, current IA of current source 72 may be applied to coupling 42 with top switch 74 closed and bottom switch 76 open to yield $+V_{DC}$. At some period of time later, current IA of current source 72 may be applied to coupling 42 with top switch 74 open and bottom switch 76 closed to yield $-V_{DC}$. In this manner, current IA will simulate AC source fluctuating between $+V_{DC}$ and $-V_{DC}$ applied across coupling 42. The example of measurement circuit 50 illustrated in FIG. 4C may function to identify the type and configuration of catheter 18 based on the known capacitance, $C_C$, of capacitor 70 in a substantially similar manner to that described with reference to the example of FIG. 4B.

Additional configurations of coupling 42 between catheter 18 and IMD 12 are contemplated. For example, coupling 42 may include optical transmitter and receiver components by which an optical signal is generated and received between, e.g., first connector 46 and second connector 48. Measurement circuit 50, alone or in conjunction with other components, including, e.g., processor 26, or a processor of another device, e.g. programmer 20, may identify catheter 18 by detecting the wavelength of the optical signal transmitted and received by coupling 42 and searching for the wavelength in a look-up table of therapy delivery components and associated resistances stored on memory 28 of IMD 12 or another device, e.g. programmer 20.

In addition to identifying catheter 18, measurement circuit 50, and, e.g., processor 26 of IMD 12, or a processor of another device may also be configured to identify a connection status between the catheter and IMD based on a signal generated as an output to an electrical input applied by circuit 50 across coupling 42. During or after implantation, catheter 18 may become partially or completely disconnected from IMD 12, in which case, continuing to pump a therapeutic fluid from the device, e.g. via pump 32 may act to deliver the fluid in unplanned dosages to unintended sites with the body of patient 16. As such, it may be useful to clinicians and patients to have awareness of the connection status between catheter 18 and IMD 12. Because changes in the connection between catheter 18 and IMD 12 may act to change the character and/or magnitude of the signal generated by coupling 42, the signal may form a basis for identifying the connection status in a manner similar to described above for identifying catheter 18 based thereon.

In one example, some part or all of first connector 46 connected to end 18A of catheter 18 may include a known electrical resistance. In such an example, connecting first connector 46 to conductor second connector 48 may act to complete measurement circuit 50 such that a voltage signal is generated as an output to an electrical input, e.g. constant current, applied by the circuit across coupling 42. However, in the event that the connection between first and second connectors 46, 48, respectively, is compromised such that the catheter 18 becomes partially or completely disconnected from IMD 12, the signal generated as an output in measurement circuit 50 will change. In such examples, measurement circuit 50, alone or in conjunction with, e.g., processor 26 of IMD 12, or a processor of another device communicatively connected to the IMD, e.g. programmer 20, may be configured to compare the output voltage directly to one or more thresholds indicative of a connection status between the IMD and catheter 18 or calculate the resistance of first connector 46 from the voltage signal and compare the resistance to the threshold(s) indicative of connection status between IMD and catheter. For example, catheter 18 may become partially disconnected from IMD 12, which may act to effectively reduce the resistance of first connector 46 of coupling 42. Processor 26 may calculate the resistance of first connector 46 from a voltage signal generated as an output to a known measurement current applied by measurement circuit 50 across coupling 42 and compare the calculated resistance to a threshold resistance to determine that catheter 18 is partially disconnected from IMD 12. In the event catheter 18 becomes completely disconnected from IMD 12 measurement circuit 50 may be broken such that the circuit does not generate any voltage signal, based upon which the circuit, alone or in conjunction with, e.g., processor 26 may identify the catheter as disconnected from the IMD.

In one example, measurement circuit 50, alone or in conjunction with, e.g., processor 26 of IMD 12, or a processor of another device may identify the connection status between catheter 18 and IMD 12 based on a signal generated as an output to an input applied by the circuit across coupling 42 as at least one of connected, disconnected, or partially disconnected. In the event, the connection status between catheter 18 and the IMD 12 is identified as one of disconnected or partially disconnected, processor 26 or another component of the IMD may be configured to generate an alert, including, e.g. an audible, tactile, or visual alert. For example, the connection status between catheter 18 and IMD 12 may be identified as partially disconnected and processor 26 may issue a sound from the IMD, or from programmer 20 in communication with the IMD. In another example, processor 26 may cause IMD 12 to vibrate within patient 16 to indicate the connection status between the IMD and catheter 18. In another example, processor 26 may communicate with programmer 20 to cause the programmer to display an alert on a display of the device that indicates that connection status between IMD 12 and catheter 18 has been identified as, e.g., partially disconnected.

Referring again to the example of FIG. 2, upon instruction from processor 26, fluid delivery pump 32 may draw fluid from reservoir 34 and pumps the fluid through internal tubing 38 to catheter 18 through which the fluid is delivered to patient 16 to effect one or more of the treatments described above, e.g., in accordance with a program stored on memory 28. Internal tubing 38 is a segment of tubing or a series of cavities within IMD 12 that run from reservoir 34, around or through fluid delivery pump 32 to catheter access port 40 and catheter 18.

Fluid delivery pump 32 can be any mechanism that delivers a therapeutic fluid in some metered or other desired flow dosage to the therapy site within patient 16 from reservoir 30 via implanted catheter 18. In one example, fluid delivery pump 32 is a squeeze pump that squeezes internal tubing 38 in a controlled manner, e.g., such as a peristaltic pump, to progressively move fluid from reservoir 34 to the distal end of catheter 18 and then into patient 16 according to parameters specified by the therapy program stored on memory 28 and executed by processor 26.

In various examples, fluid delivery pump 32 may be an axial pump, a centrifugal pump, a pusher plate pump, a piston-driven pump, or other means for moving fluid through internal tubing 38 and catheter 18. In one example, fluid delivery pump 32 is an electromechanical pump that delivers fluid by the application of pressure generated by a piston that moves in the presence of a varying magnetic field and that is configured to draw fluid from reservoir 34 and pump the fluid through internal tubing 38 and catheter 18 to patient 16.

Periodically, fluid may need to be supplied percutaneously to reservoir 34 because all of a therapeutic fluid has been or will be delivered to patient 16, or because a clinician wishes to replace an existing fluid with a different fluid or similar fluid with different concentrations of therapeutic ingredients. Refill port 26 can therefore comprise a self-sealing membrane to prevent loss of therapeutic fluid delivered to reservoir 30 via refill port 26. For example, after a percutaneous delivery system, e.g., a hypodermic needle, penetrates the membrane of refill port 26, the membrane may seal shut when the needle is removed from refill port 26.

In general, memory 28 stores program instructions and related data that, when executed by processor 26, cause IMD 12 and processor 26 to perform the functions attributed to them in this disclosure. For example, memory 28 of IMD 12 may store instructions for execution by processor 26 including, e.g., therapy programs, tables of different types of therapy delivery components and an associated measurable parameter by which each component may be uniquely identified, and any other information regarding therapy delivered to patient 16 and/or the operation of IMD 12. Memory 28 may include separate memories for storing instructions, patient information, therapy parameters, therapy adjustment information, program histories, and other categories of information such as any other data that may benefit from separate physical memory modules. Therapy adjustment information may include information relating to timing, frequency, rates and amounts of patient boluses or other permitted patient modifications to therapy.

At various times during the operation of IMD 12 to treat patient 16, communication to and from IMD 12 may be necessary to, e.g., change therapy programs, adjust parameters within one or more programs, configure or adjust a particular bolus, or to otherwise download information to or from IMD 12. Processor 26 controls telemetry module 30 to wirelessly communicate between IMD 12 and other devices including, e.g. programmer 20. Telemetry module 30 in IMD 12, as well as telemetry modules in other devices described in this disclosure, such as programmer 20, can be configured to use RF communication techniques to wirelessly send and receive information to and from other devices respectively according to, e.g., the 802.11 or Bluetooth specification sets, infrared (IR) communication according to the IRDA specification set, or other standard or proprietary telemetry protocols. In addition, telemetry module 30 may communicate with programmer 20 via proximal inductive interaction between IMD 12 and the external programmer. Telemetry module 30 may send information to external programmer 20 on a continuous basis, at periodic intervals, or upon request from the programmer.

Power source 44 delivers operating power to various components of IMD 12. Power source 44 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, traditional batteries may be used for a limited period of time. As another alternative, an external inductive power supply may transcutaneously power IMD 12 as needed or desired.

Figure 5:
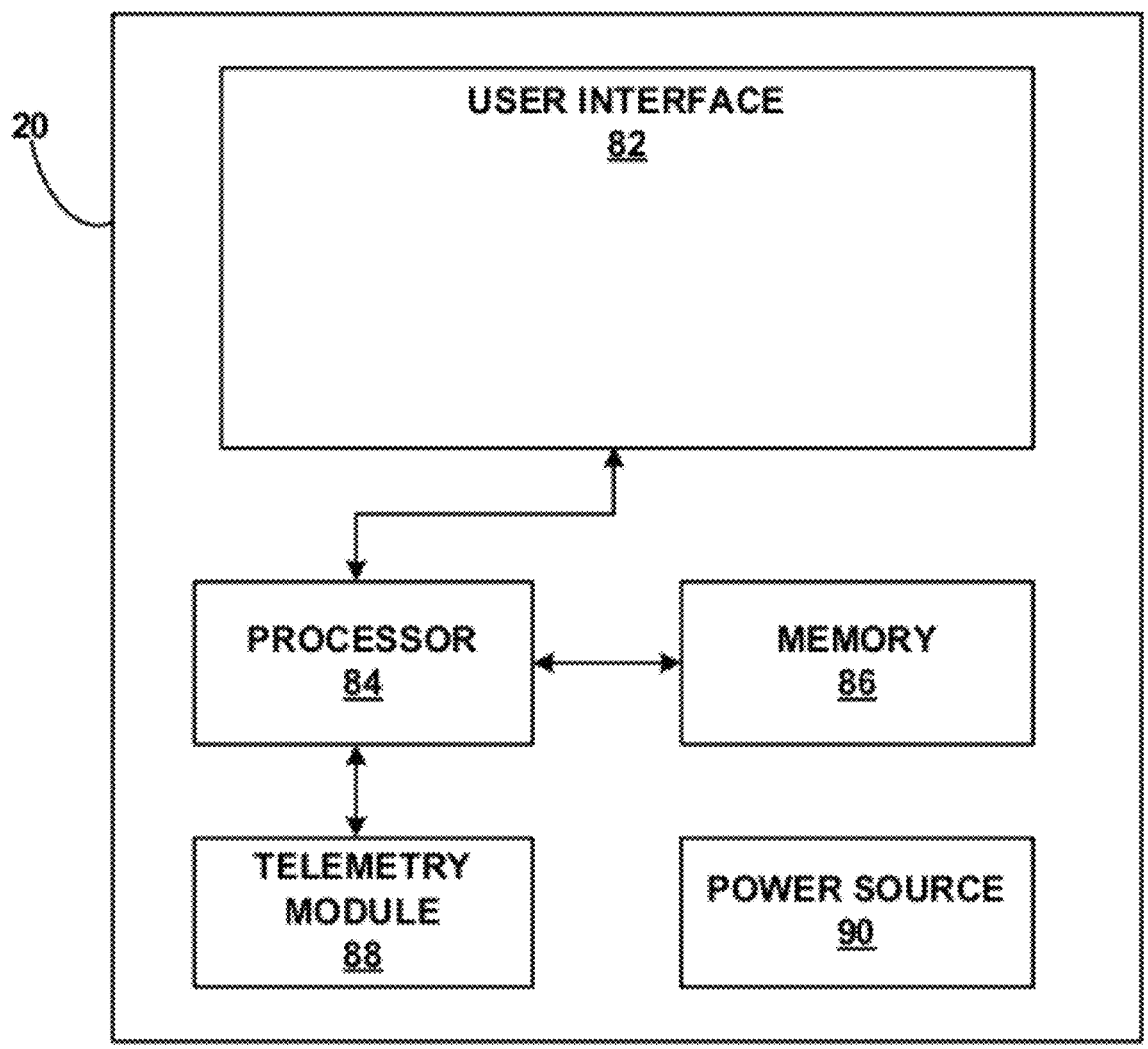
FIG. 5 is a functional block diagram illustrating an example of an external programmer shown in FIG. 1.

FIG. 5 is a functional block diagram illustrating an example of various components of external programmer 20 for IMD 12. As shown in FIG. 5, external programmer 20 may include user interface 82, processor 84, memory 86, telemetry module 88, and power source 90. A clinician or patient 16 interacts with user interface 82 in order to manually change the parameters of a therapy program, change therapy programs within a group of programs, view therapy information, view historical or establish new therapy programs, or otherwise communicate with IMD 12 or view or edit programming information. Processor 84 controls user interface 82, retrieves data from memory 86 and stores data within memory 86. Processor 84 also controls the transmission of data through telemetry module 88 to IMD 12. The transmitted data may include therapy program information specifying various therapeutic fluid delivery parameters. Memory 86 may store, e.g., operational instructions for processor 84 and data related to therapy for patient 16.

Programmer 20 may be a hand-held computing device that includes user interface 82 that can be used to provide input to programmer 20. For example, programmer 20 may include a display screen that presents information to the user and a keypad, buttons, a peripheral pointing device, touch screen, voice recognition, or another input mechanism that allows the user to navigate though the user interface of programmer 20 and provide input. In other examples, rather than being a handheld computing device or a dedicated computing device, programmer 20 may be a larger workstation or a separate application within another multi-function device.

When programmer 20 is configured for use by a clinician, user interface 82 may be used to transmit initial programming information to IMD 12 including hardware information for system 10, e.g. the type of catheter 18, the position of catheter 18 within patient 16, a baseline orientation of at least a portion of IMD 12 relative to a reference point, and software information related to therapy delivery and operation of IMD 12, e.g. therapy parameters of therapy programs stored within IMD 12 or within programmer 20, the type and amount, e.g., by volume of therapeutic fluid(s) delivered by IMD 12 and any other information the clinician desires to program into IMD 12. The clinician may use programmer 20 during a programming session to define one or more therapy programs by which IMD 12 delivers therapy to patient 16, in which case patient 16 may provide feedback to the clinician during the programming session as to efficacy of a program being evaluated or desired modifications to the program. Programmer 20 may assist the clinician in the creation/identification of therapy programs by providing a methodical system of identifying potentially beneficial therapy parameters.

Programmer 20 may also be configured for use by patient 16. When configured as a patient programmer, programmer 20 may have limited functionality in order to prevent patient 16 from altering critical functions or applications that may be detrimental to patient 16. In this manner, programmer 20 may only allow patient 16 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 16 when therapy is being delivered or when IMD 12 needs to be refilled or when the power source within programmer 20 or IMD 12 need to be replaced or recharged.

As described above, processor 84 of programmer 20 may be configured to execute one or more of the functions ascribed to processor 26 of IMD 12 in the process of identifying the type and/or configuration of catheter 18, as well as the connection status between the catheter and the IMD. Processor 84 may act in conjunction with measurement circuit 50 of IMD 12, as well as, in some examples, other components of programmer 20 and/or IMD 12, including, e.g. processor 26 and memories 28 and 86 of the IMD and programmer, respectively. For example, in the event that first connector 46 includes a known resistance and connecting catheter 18 to IMD 12 generate a voltage signal as an output to an input current applied by measurement circuit 50 across coupling 42, as described above, the circuit may function in conjunction with processor 84 of programmer 20 such that the processor calculates the resistance of first connector 46 from the voltage signal. After calculating the resistance of first connector 46 from the output voltage signal on measurement circuit 50, processor 84 may identify, e.g., the type and configuration of catheter 18 by, e.g., searching for the resistance in a look-up table or other organized aggregation of different types of therapy delivery components and associated resistances stored on memory 86 of programmer 20 or another device, e.g. memory 28 of IMD 12.

Telemetry module 88 allows the transfer of data to and from programmer 20 and IMD 12, as well as other devices, e.g. according to the RF communication techniques described above with reference to FIG. 2. Telemetry module 88 may communicate automatically with IMD 12 at a scheduled time or when the telemetry module detects the proximity of IMD 12. Alternatively, telemetry module 88 may communicate with IMD 12 when signaled by a user through user interface 82. To support RF communication, telemetry module 88 may include appropriate electronic components, such as amplifiers, filters, mixers, encoders, decoders, and the like. Programmer 20 may also communicate with another programmer or computing device via a wired or wireless connection using any of a variety of communication techniques, and/or via exchange of removable media, including, e.g., magnetic or optical disks, or memory cards or sticks including, e.g., non-volatile memory. Further, programmer 20 may communicate with IMD 12 or another device via, e.g., a local area network (LAN), wide area network (WAN), public switched telephone network (PSTN), or cellular telephone network, or any other terrestrial or satellite network appropriate for use with programmer 20 and IMD 12.

Power source 90 may be a rechargeable battery, such as a lithium ion or nickel metal hydride battery. Other rechargeable or conventional primary cell batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 12 in addition to programming IMD 12. Alternatively, a recharging device may be capable of communication with IMD 12. Then, the recharging device may be able to transfer programming information, data, or any other information described herein to IMD 12. In this manner, the recharging device may be able to act as an intermediary communication device between external programmer 20 and IMD 12.

Figure 6:
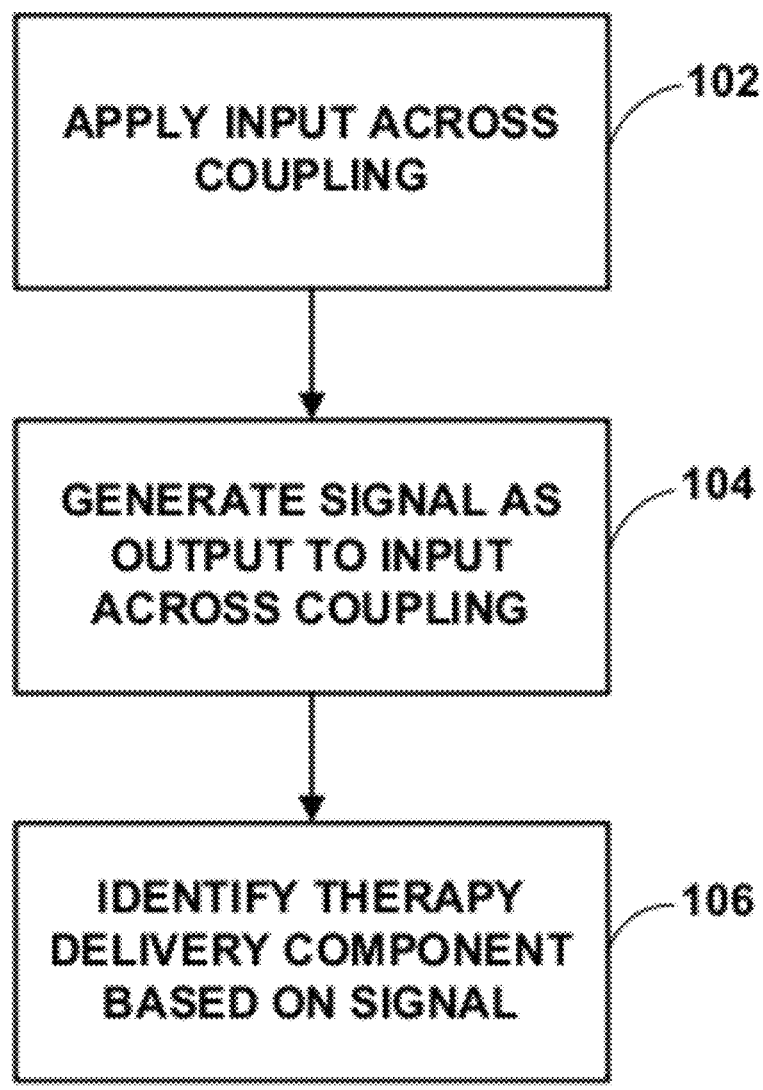
FIG. 6 is a flow chart illustrating an example method of identifying a therapy delivery component.

FIG. 6 is a flow chart illustrating an example method of identifying a therapy delivery component connected to an IMD. The method of FIG. 5 includes applying an electrical input across a coupling between an IMD and a therapy delivery component (100), generating an electrical signal as an output to the input applied across the coupling (102) and identifying the therapy delivery component based on the output electrical signal (104). The functions of the method of FIG. 6 are described as executed by IMD 12, and in particular, measurement circuit 50, alone or in conjunction with, e.g., processor 26 and memory 28 of IMD 12. However, in other examples, one or more of these functions may be carried out by and/or in conjunction with other devices including, e.g., external programmer 20.

In one example, the method of FIG. 5 includes applying an electrical input across a coupling between an IMD and a therapy delivery component (100). For example, battery 60 of measurement circuit 50 may supply power to constant current source 62, which drives measurement circuit 50 with a known current, I. Connecting IMD 12 and catheter 18 via coupling 42 may act to complete measurement circuit 50 such that current, I, from current source 62 may flow across conductor 46, which includes a known resistance, $R_C$. Thus, current source 62 of measurement circuit 50 applies input constant current, I, across conductor 46 of coupling 42.

The method of FIG. 6 also includes generating a signal as an output to the input applied across the coupling between an IMD and therapy delivery component (102). As illustrated in the examples of FIGS. 2 and 3, catheter 18 may be connected to IMD 12 by coupling 42. In one example, some part or all of coupling 42 may include a known electrical or other characteristic, including, e.g., a known resistance. Connecting IMD 12 and catheter 18 via coupling 42 may act to complete measurement circuit 50 such that a voltage signal is generated as an output to the current input applied by the measurement circuit across the coupling. For example, voltmeter 64 of measurement circuit may be configured to produce an output voltage signal, $V_O$, when current, I, from current source 62 is applied across coupling 42, and, in particular, across conductor 46 including resistance, $R_C$.

In addition to generating the output electrical signal (102), the method of FIG. 6 may include identifying the catheter based on the output electrical signal (104). In one example, measurement circuit 50 may identify catheter 18 connected to IMD 12 based on the output voltage, $V_O$. For example, measurement circuit 50 may communicate output voltage, $V_O$, from voltmeter 64 to a processor, e.g. via an ADC. In one example, the processor and other digital components necessary to identify catheter 18 based on the analog electrical output signals generated by measurement circuit 50 may be included in the measurement circuit. In another example, however, measurement circuit 50 may communicate with, e.g., processor 26 and memory 28 in the process of identifying the type and configuration of catheter 18. In one example, processor 26 of IMD 12 cross-references the voltage, $V_O$, to the resistance, $R_C$, of conductor 46a of first connector 46 of coupling 42, e.g., in a look-up table or other organized aggregation of data of therapy delivery components and associated resistances stored on memory 28.

In another example, measurement circuit 50 may communicate the output voltage signal, $V_O$, from voltmeter 64 to processor 26, which may identify the type and configuration of catheter 18 by calculating the resistance, $R_C$, of conductor 46a of first connector 46 from the voltage. For example, processor 26 may calculate the resistance of conductor 46a of first connector 46 from the voltage, $V_O$, generated as an output to the input current, I, applied by current source 62 of measurement circuit 50 across coupling 42 and search for the resistance in a look-up table or other organized aggregation of data of therapy delivery components and associated resistances stored on memory 28 of the IMD 12, or memory of another device, e.g. programmer 20. In some examples, measurement circuit 50, alone or in conjunction with other components, e.g. processor 26, or a processor of another device, may identify characteristics of catheter 18 other than those described above. In one example, measurement circuit 50 may identify whether or not catheter 18 is safe for use with other medical equipment, including, e.g., a Magnetic Resonance Imaging (MRI) machine.

In some examples, the method of FIG. 6 may also include identifying a connection status between the IMD and therapy delivery component based on the signal generated at the connection. For example, the method of FIG. 6 may include identifying a connection status between catheter 18 and IMD 12 based on a signal generated as an output to an electrical input applied by measurement circuit 50 across coupling 42. The connection status between IMD 12 and catheter 18 may be identified as, e.g., one of connected, disconnected, or partially disconnected. In one example, coupling 42 may include a known electrical resistance. In such an example, connecting catheter 18 to IMD 12 via coupling 42 may act to complete measurement circuit 50 such that a voltage signal is generated as an output to an input, e.g. current input applied across coupling 42 by the measurement circuit. However, in the event that the connection at coupling 42 is compromised such that the catheter 18 becomes partially or completely disconnected from IMD 12, the output voltage signal generated by measurement circuit 50 will change.

In such examples, measurement circuit 50, alone or in conjunction with, e.g., processor 26 of IMD 12, or a processor of another device communicatively connected to the IMD, e.g. programmer 20, may be configured to compare the output voltage directly to one or more thresholds indicative of a connection status between the IMD and catheter 18 or calculate the resistance of first connector 46 from the voltage signal and compare the resistance to the threshold(s) indicative of connection status between IMD and catheter. For example, catheter 18 may become partially disconnected from IMD 12, which may act to effectively reduce the resistance of first connector 46 of coupling 42. Processor 26 may calculate the resistance of first connector 46 from a voltage signal generated as an output to a constant current applied by measurement circuit 50 across coupling 42 and compare the calculated resistance to a threshold resistance to determine that catheter 18 is partially disconnected from IMD 12. In the event catheter 18 becomes completely disconnected from IMD 12 measurement circuit 50 may be broken such that the circuit does not generate any voltage signal, based upon which the circuit, alone or in conjunction with, e.g., processor 26 may identify the catheter as disconnected from the IMD.

The method of FIG. 6 may also include generating an alert if the connection status between IMD 12 and catheter 18 is identified as one of disconnected or partially disconnected. In one example, measurement circuit 50, alone or in conjunction with, e.g., processor 26 of IMD 12, or a processor of another device may identify the connection status between catheter 18 and IMD 12 based on a signal generated as an output to an input applied by the circuit across coupling 42 as at least one of connected, disconnected, or partially disconnected. In the event, the connection status between catheter 18 and the IMD 12 is identified as one of disconnected, or partially disconnected, processor 26 or another component of the IMD may be configured to generate an alert, including, e.g. an audible, tactile, or visual alert. For example, the connection status between catheter 18 and IMD 12 may be identified as partially disconnected and processor 26 may issue a sound from the IMD, or from programmer 20 in communication with the IMD. In another example, processor 26 may cause IMD 12 to vibrate within patient 16 to indicate the connection status between the IMD and catheter 18. In another example, processor 26 may communicate with programmer 20 to cause the programmer to display an alert on a display of the device that indicates that connection status between IMD 12 and catheter 18 has been identified as, e.g., partially disconnected.

Although the foregoing examples are described with reference to a fluid delivery device connected to a catheter and configured to deliver a therapeutic fluid to a patient, the techniques for identifying therapy delivery components disclosed are equally applicable to other types of medical devices. For example, the disclosed techniques may be employed to identify medical leads, including, e.g., electrical stimulation leads connected to an implantable pulse generator (IPG) configured to deliver electrical stimulation to a patient via electrodes connected to the lead. The IPG and lead may be configured to deliver neurostimulation, e.g. spinal cord stimulation (SCS), peripheral nerve field stimulation (PNFS), peripheral nerve stimulation (PNS), deep brain stimulation (DBS), cardiac stimulation, occipital nerve stimulation (OCS), and other types of electrical stimulation.

Figure 7:
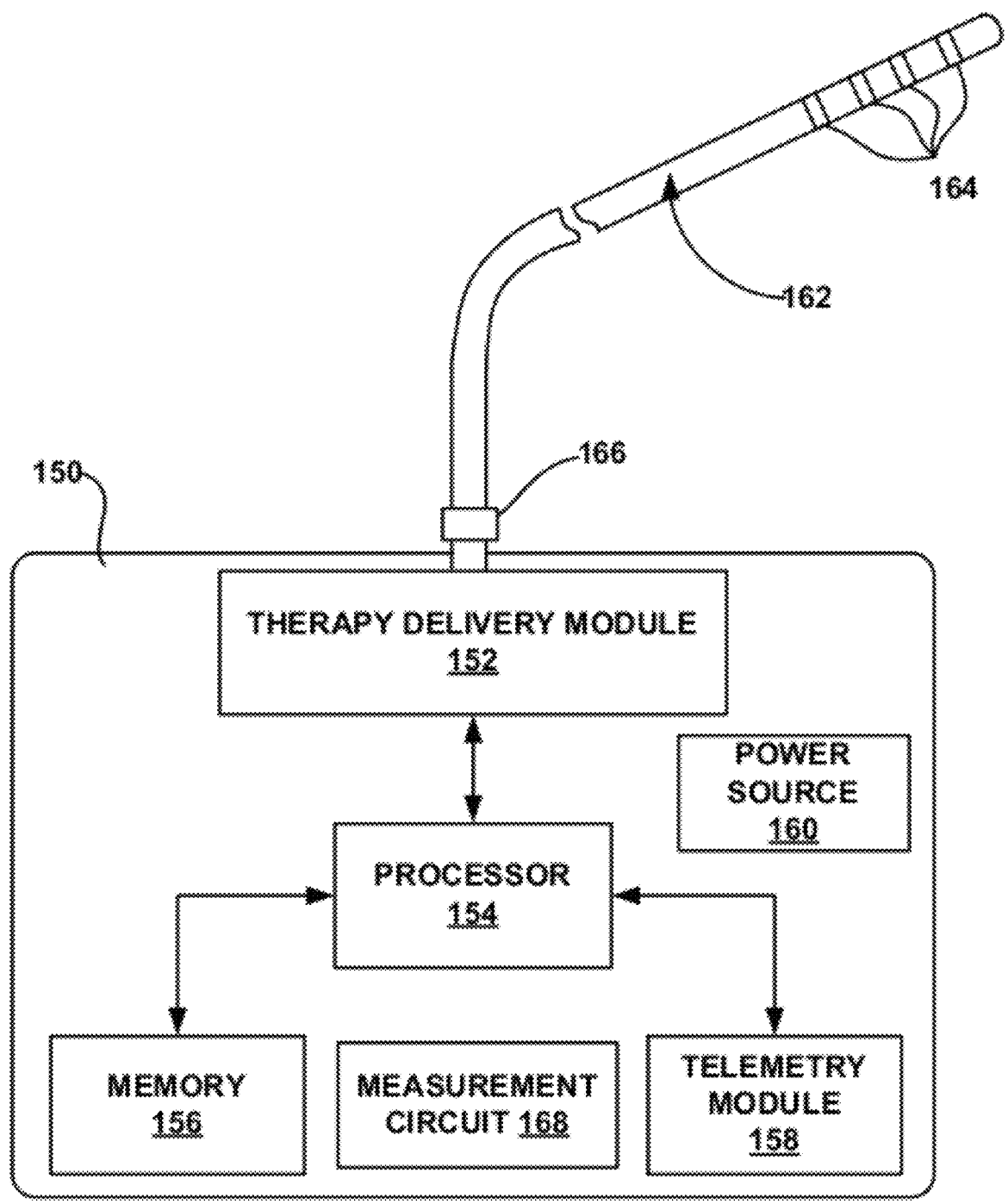
FIG. 7 is functional block diagram illustrating an example implantable pulse generator and medical lead.

For example, FIG. 7 is a functional block diagram illustrating example IPG 150 including therapy delivery module 152, processor 154, memory 156, telemetry module 158, power source 160, and measurement circuit 168. Lead 162, including electrodes 164 connected thereto, is connected to IMD 150 via coupling 166. Lead 162 may, in some examples, include internal conductor(s) connecting electrodes 164 to therapy delivery module 152. Processor 154 therapy delivery module 152 to deliver electrical stimulation to a patient via electrodes 164 on lead 162. Processor 154 may also, e.g., retrieve data from and stores data within memory 156 and control the transmission of data through telemetry module 158 to and from IPG 150. The transmitted data may include therapy program information specifying various electrical stimulation parameters. Memory 156 may store, e.g., operational instructions for processor 154 and data related to therapy delivered to patient 16 via therapy delivery module 154.

In the example of FIG. 7, lead 162 is connected to IPG 150 by coupling 166 that has a known physical property, e.g. electrical resistance or capacitance, based upon which the type and particular configuration of the therapy delivery component may be identified. In one example, coupling 166 between lead 162 and IPG 150 may include a first connector connected to a proximal end of the lead, i.e. an end closest to the IPG. Some part or all of the first connector of coupling 166 connected to lead 162 may include a known electrical resistance. Coupling 166 may also include a second connector connected to IPG 150 and measurement circuit 168 of the IPG. The second connector of coupling 166 may be configured to receive the first connector connected to lead 162. In such an example, connecting the first connector connected to lead 162 with the second connector connected to IPG 150 may act to complete measurement circuit 168 such that a voltage signal is generated as an output to an electrical input, e.g. current input applied by the measurement circuit across coupling 166. Measurement circuit 168, alone or in conjunction with other components, e.g., processor 154 may then identify lead 162 directly based on the output voltage or by calculating the resistance of the first connector of coupling 166 from the voltage. For example, measurement circuit 168 may generate the output voltage and transmit the voltage to processor 154, e.g. via an ADC. Processor 154 may then, e.g., calculate the resistance of the first connector from the voltage output by measurement circuit 168 and search for the resistance in a look-up table or other organized aggregation of data of therapy delivery components and associated resistances stored on memory 156.

In other examples, the first connector of coupling 166 between lead 162 and IPG 150 may include a known capacitance instead of resistance, by which, in a similar fashion as described in the foregoing example, the type and particular configuration of the lead connected to the IPG may be identified. Additional configurations of the coupling between a medical and an IPG are also possible, including, e.g. a coupling including optical components configured to generate optical signals that may be employed to identify a lead connected to an IPG.

Figure 8:
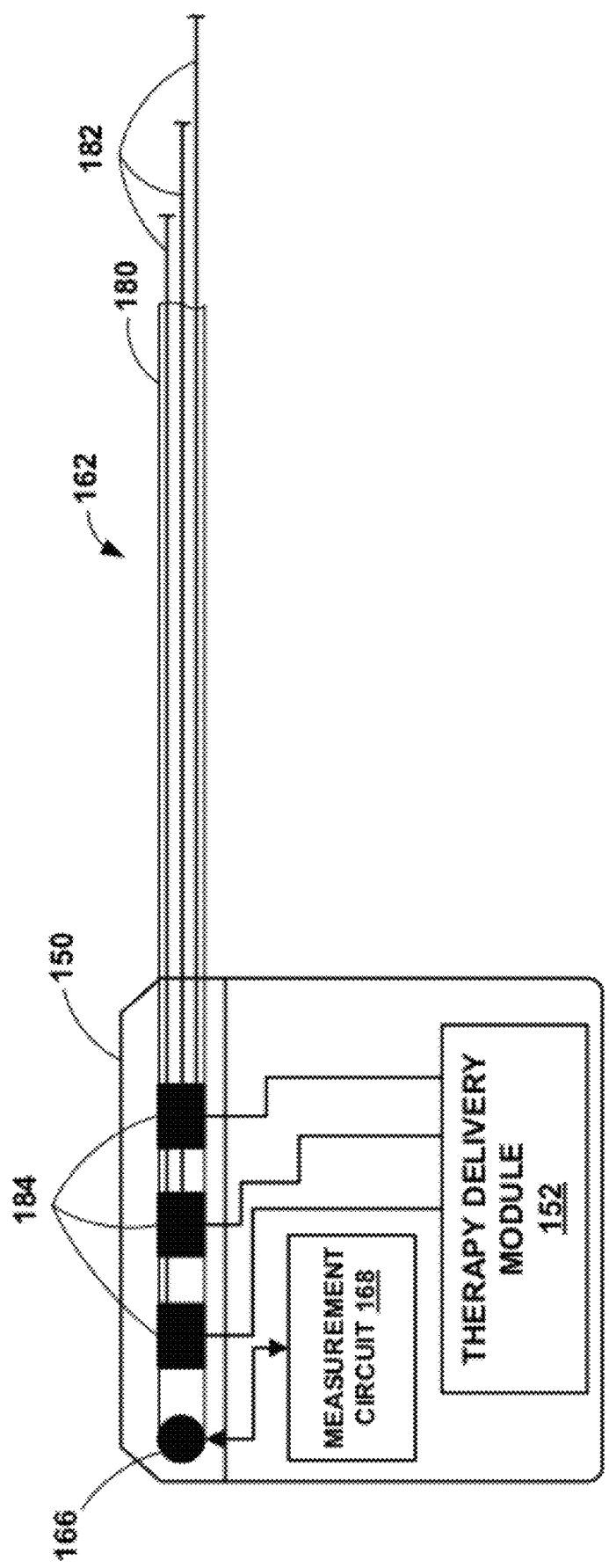
FIG. 8 is a conceptual diagram illustrating an example configuration of the implantable pulse generator and lead of FIG. 7.

Because lead 162 conducts electricity to electrodes 164 in the example IPG 150 of FIG. 7, coupling 166 may need to be designed such that it does not to modify the electrode-conductor impedances of the lead, because electrical stimulation is delivered by therapy delivery module 152 to patient 16 via those paths. As such, coupling 166 may require conductive elements separate from the elements conducting electricity between IPG 150, lead 162, and electrodes 164. FIG. 8 is a conceptual diagram illustrating an example configuration of the manner in which coupling 166 may connect lead 162 to IPG 150 without disturbing or modifying the electrical connections conducting electricity between IPG 150, lead 162, and electrodes 164. In FIG. 8, lead 162 includes lead body 180, conductors 182, and ring contacts 184. Conductors 182 run the length of lead 162 and are electrically coupled toward the distal end of the lead to respective ones of electrodes 164 (not shown). At the proximal end of lead 162, each conductor 182 is connected to a respective ring contact 182. The proximal end of lead 162 is received by IPG 150 such that each of ring contacts 184 couple with corresponding electrical contacts on the IPG, thereby connecting electrodes 164 to therapy delivery module 152.

In the example of FIG. 8, coupling 166 connects the proximal end of lead 162 to IPG 150 via an electrical connection that is separate from the connection between electrodes 164 and therapy delivery module 152, i.e. conductors 182 and ring contacts 184. Coupling 166 may include an electrical contact on lead 162 that engages a contact on IPG 150 such that connecting lead 162 to IPG 150 functions to complete measurement circuit 168, which may, in turn, cause a voltage signal to be generated as an output to an electrical input, e.g. current input applied by the measurement circuit across coupling 166. Other physical examples of coupling 166 are contemplated by this disclosure. For example, coupling 166 may be located somewhere other than the proximal end of lead 162, as shown in the example of FIG. 8.

Although the target therapy delivery site described with reference to the foregoing examples is proximate to the spinal cord of a patient, other applications of therapy systems in accordance with this disclosure include alternative delivery sites. In some examples, the target delivery site may be proximate to different types of tissues including, e.g., nerves, e.g. sacral, pudendal or perineal nerves, organs, muscles or muscle groups. In one example, a catheter may be positioned to deliver a therapeutic fluid to a deep brain site or within the heart or blood vessels. Delivery of a therapeutic fluid within the brain may help manage a number of disorders or diseases including, e.g., chronic pain, diabetes, depression or other mood disorders, dementia, obsessive-compulsive disorder, migraines, obesity, and movement disorders, such as Parkinson's disease, spasticity, and epilepsy. A catheter may also be positioned to deliver insulin to a patient with diabetes. In other examples, the system may deliver a therapeutic fluid to various sites within a patient to facilitate other therapies and to manage other conditions including peripheral neuropathy or post-operative pain mitigation, ilioinguinal nerve therapy, intercostal nerve therapy, gastric drug induced stimulation for the treatment of gastric motility disorders and/or obesity, and muscle stimulation, or for mitigation of peripheral and localized pain e.g., leg pain or back pain.

The techniques described in this disclosure for identifying therapy delivery components may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

The invention claimed is:
1. A system comprising:
an implantable medical device (IMD);
a therapy delivery component configured to deliver therapy to a patient;
a coupling connecting the therapy delivery component to the IMD; and
a measurement circuit configured to apply an electrical input across the coupling and identify the therapy delivery component based on an electrical signal generated as an output upon application of the input across the coupling.
2. The system of claim 1, wherein the coupling comprises:
a first connector connected to an end of the therapy delivery component, wherein the first connector has an electrical resistance; and
a second connector connected to the IMD and the measurement circuit and configured to receive the first connector.
3. The system of claim 2, wherein the measurement circuit is configured to apply the electrical input to the second connector and the electrical signal generated as an output upon application of the input across the coupling comprises a voltage generated when the first connector is connected to the second connector, and wherein the measurement circuit identifies the therapy delivery component based on the voltage.
4. The system of claim 3, wherein the measurement circuit identifies the therapy delivery component by calculating the resistance of the first connector from the voltage.
5. The system of claim 1, wherein the coupling comprises:
a first connector connected to an end of the therapy delivery component;
a second connector connected to the IMD and the measurement circuit and configured to receive the first connector; and
a dielectric interposed between the first and the second connectors.
6. The system of claim 5, wherein the measurement circuit is configured to apply the electrical input to the second connector and the electrical signal generated as an output upon application of the input across the coupling comprises a voltage generated when the first connector is connected to the second connector, and wherein the measurement circuit identifies the therapy delivery component based on the voltage.
7. The system of claim 1, wherein the processor is configured to determine compatibility of the therapy delivery component with a Magnetic Resonance Imaging (MRI) system.

8. The system of claim 1, wherein the therapy delivery component comprises at least one of a catheter or an electrical stimulation lead.

9. The system of claim 1, wherein the electrical input comprises at least one of a constant current or a constant voltage input.

10. A method comprising:
applying an electrical input across a coupling between an implantable medical device (IMD) and a therapy delivery component configured to deliver therapy to a patient;
generating an electrical signal as an output to the electrical input applied across the coupling; and
identifying the therapy delivery component based on the electrical signal.

11. The method of claim 10, wherein the coupling comprises:
a first connector connected to an end of the therapy delivery component and comprising a resistance; and
a second connector connected to the IMD and configured to receive the first connector.

12. The method of claim 11, wherein generating the output electrical signal comprises generating a voltage signal when the first connector is connected to the second connector as an output to an input current applied across the first connector, and wherein identifying the therapy delivery component comprises identifying the therapy delivery component based on the voltage.

13. The method of claim 10, wherein the coupling comprises:
a first connector connected to an end of the therapy delivery component;
a second connector connected to the IMD and configured to receive the first connector; and
a dielectric interposed between the first and the second connectors.

14. The method of claim 13, wherein generating the output electrical signal comprises generating a voltage signal when the first connector is connected to the second connector as an output to an input current applied across the first connector, and wherein identifying the therapy delivery component comprises identifying the therapy delivery component based on the voltage.

15. The method of claim 10 further comprising determining compatibility of the therapy delivery component with a Magnetic Resonance Imaging (MRI) system based on the electrical signal generated as an output to the electrical input applied across the coupling.

16. The method of claim 10, wherein the therapy delivery component comprises at least one of a catheter or a medical lead.

17. A system comprising:
means for applying an electrical input across a coupling between an implantable medical device (IMD) and a therapy delivery component configured to deliver therapy to a patient;
means for generating an electrical signal as an output to the electrical input applied across the coupling between an implantable medical device (IMD) and a therapy delivery component configured to deliver therapy to tissue of a patient; and
means for identifying the therapy delivery component based on the electrical signal.

18. A system comprising:
an implantable medical device (IMD);
a therapy delivery component configured to deliver therapy to a patient;
a coupling connecting the therapy delivery component to the IMD; and
a measurement circuit configured to apply an electrical input across the coupling and identify a connection status between the IMD and the therapy delivery component based on an electrical signal generated as an output upon application of the input across the coupling.

19. The system of claim 18, wherein the connection status between the IMD and the therapy delivery component comprises at least one of connected, disconnected, or partially disconnected.

20. The system of claim 19 further comprising a processor connected to the measurement circuit, and wherein the processor is configured to receive the connection status from the measurement circuit and generate an alert when the connection status between the IMD and the therapy delivery component comprises at least one of disconnected or partially disconnected.

21. The system of claim 20, wherein the alert comprises at least one of an audible, tactile, or visual alert.

22. The system of claim 20 further comprising a programmer communicatively connected to the IMD, wherein the programmer comprises the processor.

23. A method comprising:
applying an electrical input across a coupling between an implantable medical device (IMD) and a therapy delivery component configured to deliver therapy to a patient;
generating an electrical signal as an output to the electrical input applied across the coupling; and
identifying a connection status between the IMD and the therapy delivery component based on the electrical signal.

24. The method of claim 23, wherein the connection status between the IMD and the therapy delivery component comprises at least one of connected, disconnected, or partially disconnected.

25. The method of claim 23 further comprising generating an alert when the connection status between the IMD and the therapy delivery component comprises at least one of disconnected or partially disconnected.

26. The method of claim 25, wherein the alert comprises at least one of an audible, tactile, or visual alert.

27. A system comprising:
means for applying an electrical input across a coupling between an implantable medical device (IMD) and a therapy delivery component configured to deliver therapy to a patient;
means for generating an electrical signal as an output to the electrical input applied across the coupling between an implantable medical device (IMD) and a therapy delivery component configured to deliver therapy to tissue of a patient; and
means for identifying a connection status between the IMD and the therapy delivery component based on the electrical signal.

* * * * *